United States Patent [19]

Casale

[11] 4,437,489

[45] Mar. 20, 1984

[54] GAS FLOW CONTROLLER

[75] Inventor: Michael A. Casale, Newark, Del.

[73] Assignee: Hewlett-Packard Company, Palo Alto, Calif.

[21] Appl. No.: 334,417

[22] Filed: Dec. 24, 1981

[51] Int. Cl.³ .............................................. F16K 31/02
[52] U.S. Cl. ................................... 137/487.5; 137/8; 137/12; 137/557
[58] Field of Search .................. 137/487.5, 8, 12, 557; 73/702

[56] References Cited

U.S. PATENT DOCUMENTS

4,373,549  2/1983  Nalepa et al. ..................... 137/487.5

Primary Examiner—A. Michael Chambers
Attorney, Agent, or Firm—Donald N. Timble

[57] ABSTRACT

A flow controller having a volume, a pressure transducer coupled to said volume, a first valve coupled between a source of gas under pressure and said volume, a second valve coupled between said volume and a reference volume, a third valve coupled between said reference volume and a load wherein said valves are cyclically operated so as to permit gas to flow through said volumes to a load and wherein maximum and minimum pressures are measured with said first and second valves closed.

4 Claims, 2 Drawing Figures

GAS FLOW CONTROLLER

PRIOR ART

This invention is an improvement on one of the specie for controlling gas flow between a pressurized source and a load that is described in the U.S. patent application, Ser. No. 011,333, entitled "Mass Flow/Pressure Control System" which was filed on Feb. 12, 1979, for Roger A. Nalepa et al. now U.S. Pat. No. 4,373,549, issued Feb. 15, 1983, and which will be assigned to the same assignee as that patent application.

In the pertinent specie of the flow control system described in the above-identified patent application, gas from a pressurized source is cylically applied to a first chamber and coupled from the first chamber to a load via a second chamber. Means including a transducer coupled to the first chamber are provided for deriving signals representing the maximum pressure $P_A$ and the minimum pressure $P_B$ occurring therein during each cycle. The actual flow m was determined from the expression $$[(P_A - P_B)V]/\Delta t RT \qquad (1)$$

wherein V is the volume of the first chamber, $\Delta t$ is the duration of a cycle, R is the universal gas constant and T is the absolute temperature of the gas. The flow was compared with a desired mass flow and the difference was used to control the flow of gas into the first chamber. Alternatively, either the maximum pressure $P_A$ or the minimum pressure $P_B$ could be controlled by respectively comparing them with desired values and using the difference to control the flow of gas into the first chamber.

In order to increase the accuracy of the signals representing $P_A$ and $P_B$, means were provided for the purpose of holding them constant while the signals representing them were derived. This was achieved for low cyclic frequencies by cutting off the first chamber from the gas supply and the second chamber while the signals representing $P_A$ were being derived and by cutting off the series-coupled first and second chambers from the source of gas and load while the signals representing $P_B$ were being derived. Whereas both $P_A$ and $P_B$ were constant at low cyclic frequencies, it was found that $P_B$ varied during each cycle at the higher cyclic frequencies that are required to increase the resolution of the control. Such a change in $P_B$ was an error and resulted in an erroneous control of mass flow or of pressure. This was surprising in view of the fact that the fixed volume of both chambers was coupled to the transducer.

BRIEF DISCUSSION OF THE INVENTION

Applicant has discovered that gas entering either chamber causes a change in temperature that gradually reverts to a steady value as heat passes through the walls of the chamber and that pressure signals derived before the steady value was reached would be in error. Because of the shape and small volume of the first chamber, the temperature attained a steady value before the signals representing the maximum value $P_A$ were derived so that $P_A$ was constant while it was being measured; but the shape of the second chamber caused the gas to be distributed farther from its walls and its volume was greater so that the temperature therein did not reach a steady value prior to the period when the signals representing the minimum pressure $P_B$ were being derived. Because both chambers are coupled to the transducer during this period, the output valve between them being open, any error in pressure in the second chamber due to the fact that its temperature was not stabilized affected the pressure seen by the transducer and caused the signals representing the minimum pressure $P_B$ to be in error.

In accordance with this invention, the errors are eliminated without reducing resolution by closing the output valve between the two chambers during the period when the signals representing the minimum pressure $P_B$ are being derived. The first chamber is therefore coupled to the transducer, but the second chamber is not, so that any effect on pressure that the unstabilized temperature in the second chamber would otherwise have is eliminated.

DETAILED DESCRIPTION OF THE INVENTION

Figure 1:
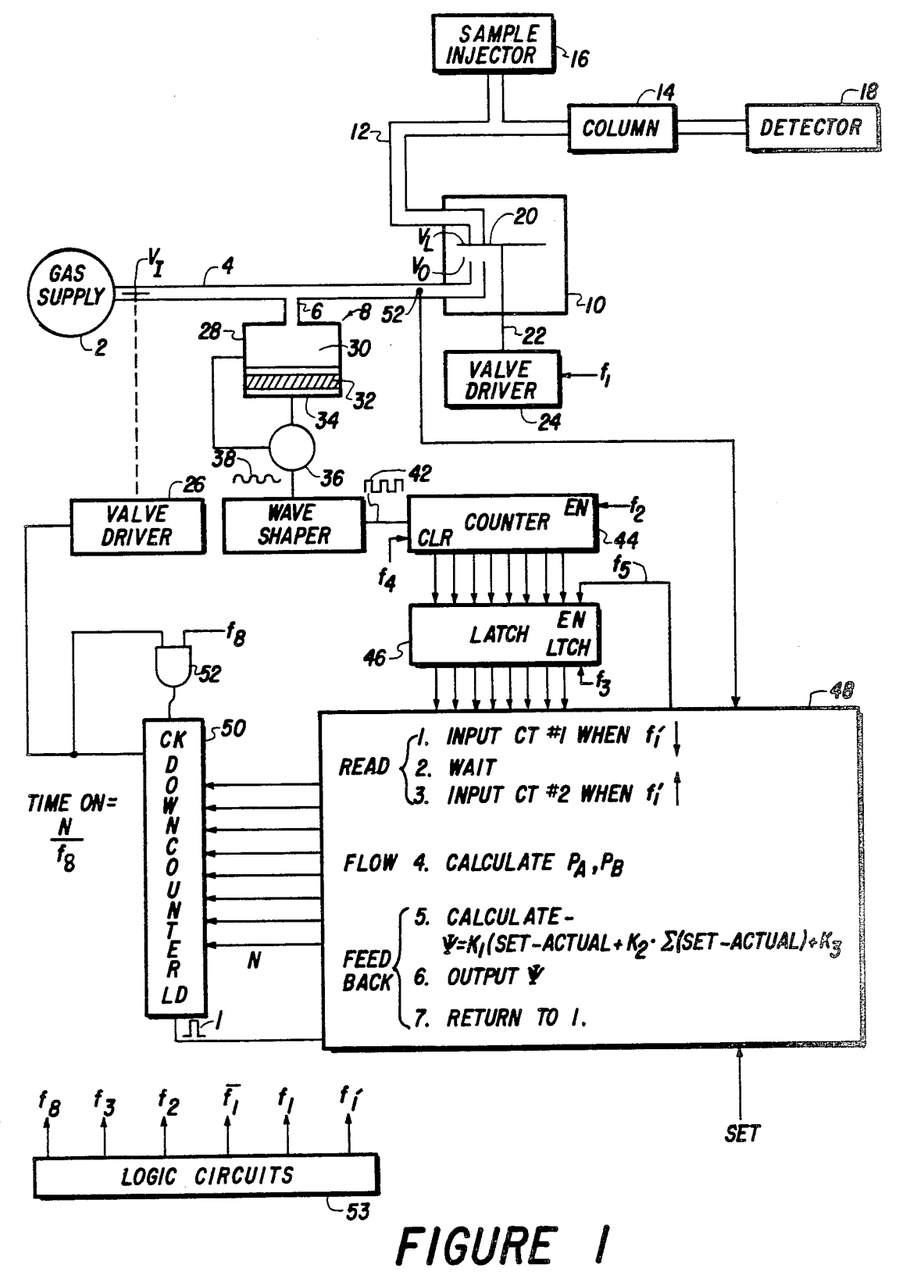
FIG. 1 is a schematic diagram of a gas flow control system embodying the invention.

In FIG. 1, a supply 2 of pressurized gas is coupled to an input valve $V_I$ that is connected by a tube 4 to an output valve $V_O$. A tube 6 connects a pressure transducer 8 to the tube 4. The portion of the tube 4 between the valves $V_I$ and $V_O$, the tube 6 and the space inside the transducer 8 that is in communication with the tube 6 define a first chamber. A second chamber 10 is coupled to the output valve $V_O$ and a load valve $V_L$ connects the second chamber 10 via a tube 12 to a load which may be the column 14 of a gas chromatograph having a sample injector 16 and a detector 18. As illustrated, the valves $V_O$ and $V_L$ are comprised of opposing ends of the tubes 4 and 12 and a plate 20 that is mounted on a rod 22. The valve $V_L$ is closed and the valve $V_O$ opened by moving the rod 22 up with a driver 24 so that the plate 20 blocks the end of the tube 12 and leaves the end of the tube 4 open. The output valve $V_O$ is closed and the valve $V_L$ opened by moving the rod 22 down with the driver 24 so that the plate 20 blocks the end of the tube 4 and leaves the end of the tube 12 open. As is apparent, the valves $V_O$ and $V_L$ could be entirely separate. The input valve $V_I$ is controlled by a valve driver 26.

Means including the pressure transducer 8 are provided for producing electrical signals representing pressure in the first chamber. Although the transducer 8 may be one of many types, it is shown as being comprised of a cylindrical metal tank 28 having a flexible bottom 30 that can bend up or down in response to the pressure of the gas in the tank 28. A disc 32 of insulating material is firmly attached to the bottom of the inside walls of the tank 28, and a metal disc 34 is adhered to the bottom of the disc 32 so as to form a variable capacitor having a capacitance depending on the distance between the bottom 30 of the tank 28 and the disc 32. By electrically coupling the tank 28 and the disc 34 to the tuned circuit, not shown, of an oscillator 36, fluctuations in the capacitance caused by the gas pressure in the first chamber vary the frequency of the oscillator. The output of the oscillator 36, which is generally sinusoidal in shape, as indicated by a wave 38, is coupled to a wave-shaping circuit 40 that amplifies and clips the output of the oscillator 36 so as to form square waves, as indicated at 42.

The square waves 42 are applied to a counter 44 that is turned on when a wave $f_2$ applied to its "enable" input is high. While enabled, the counter 44 counts the number of cycles in the square wave 42 and supplies a corresponding digital number to a latch 46. The average pressure occurring while the counter 44 is turned on is proportional to the number of cycles counted. The latch 46 acquires the digital number at the output of the counter 44 in response to a wave $f_3$ applied to its latch terminal. After this, the counter 44 may be cleared by a wave $f_4$ applied to its "clear" terminal. The digital output of the latch 46 is conducted to a computer 48 when the computer supplies a wave $f_5$ to the "enable" terminal of the latch 46.

The desired pressure or mass flow is introduced into the computer 48 via a SET input. In a manner to be explained, the computer 48 calculates a number N corresponding to the time the input valve $V_I$ is to be open. The input of a downcounter 50 is coupled so as to receive the number N when a load pulse l is applied to its load terminal from the computer 48. As long as the count in the downcounter 50 is other than zero, its output is high so as to cause the valve driver 26 to which it is coupled to keep the input valve $V_I$ open. The output of the downcounter 50 is connected to one input of an adder 52, pulses $f_8$ are applied to the other input, and the output is connected to the clock input of the downcounter 50. Thus, as long as there is a count in the downcounter 50, the adder 52 will go high at each pulse of $f_8$ and lower the count in the downcounter by one. The output of the downcounter 50 is also connected to the valve driver 26. As long as the output of the downcounter 50 is high, the input valve $V_I$ will be fully open. The various waves, $f_1$, $f_1'$, $f_1$, $f_2$, $f_3$, $f_4$, $f_5$ and $f_8$ are derived in any suitable manner by logic circuits 53.

OPERATION

Figure 2:
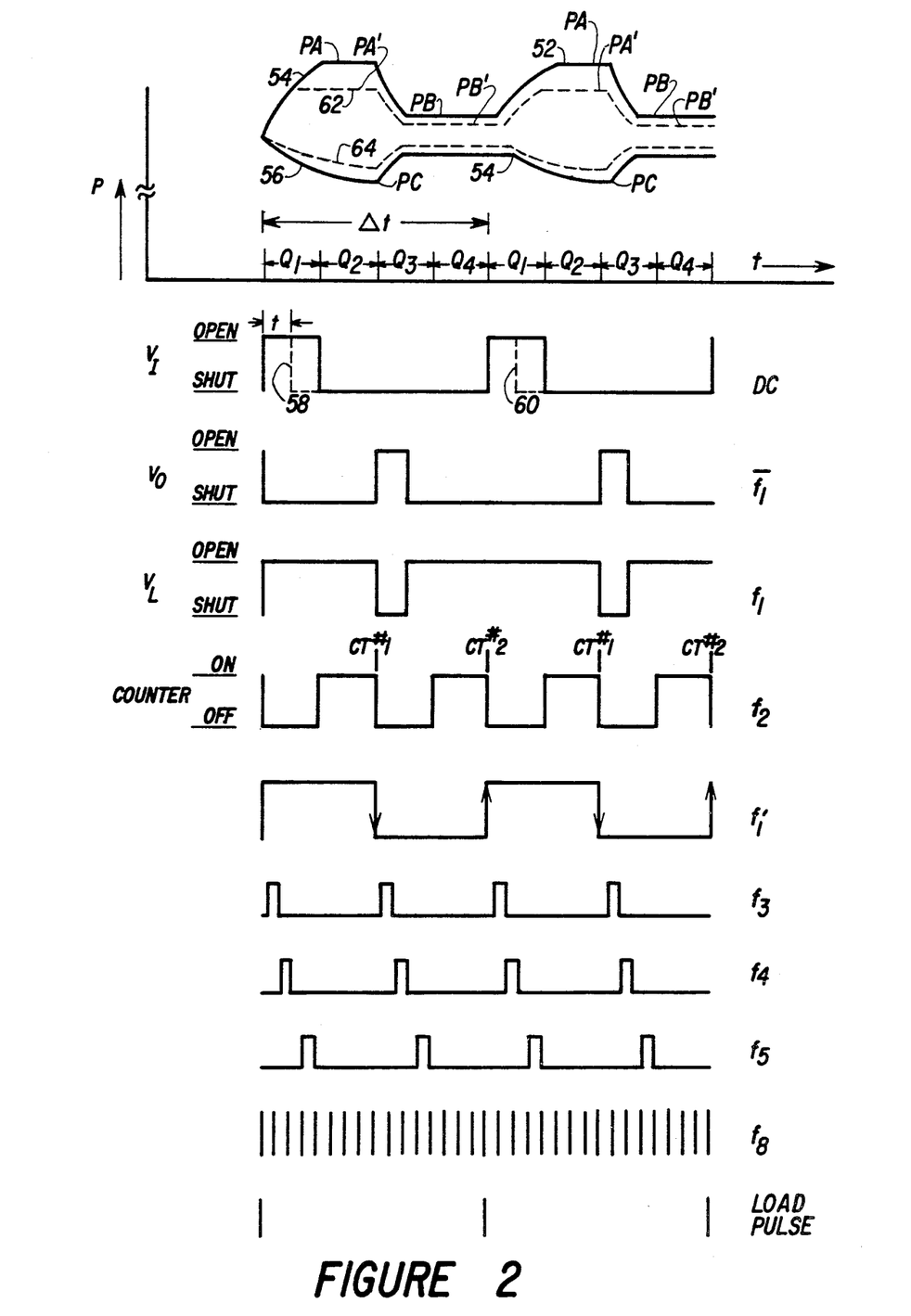
FIG. 2 is a series of diagrams illustrating the operation of FIG. 1.

Reference is now made to FIG. 2 wherein the timing of the open and shut positions of the input valve $V_I$, the output valve $V_O$ and the load valve $V_L$ are respectively indicated by the waves DC, $f_1$ and $f_1$. The variation in pressure in the first chamber that occurs when $V_I$ is open for the entire first quarter of an interval $\Delta t$ is illustrated by the solid line 54 in the pressure graphs P, and the corresponding variation in pressure in the second chamber 10 is illustrated by the solid line 56. If the input valve $V_I$ is open for only a part of the first quarter $Q_1$ of an interval $\Delta t$, as indicated by the dashed lines 58 and 60 of the wave DC, the pressure variation in the first chamber is as indicated by the dashed line 62 of the pressure graphs P, and the pressure variation in the second chamber 10 is as indicated by the dashed line 64. As shown in the wave $f_2$, the counter 44 is turned on during the quarters $Q_2$ and $Q_4$ of each interval $\Delta t$ and the counts Ct#1 and Ct#2 are respectively attained at the ends of these quarters. Ct#1 is proportional to the maximum pressure $P_A$ and Ct#2 is proportional to the minimum pressure $P_B$ if the input valve $V_I$ is open for the entire first quarter $Q_4$ of each interval; and the counts Ct#1 and Ct#2 are respectively proportional to the lesser pressures $P_A'$ and $P_B'$ if the input valve $V_I$ closes at the times indicated by the dashed lines 58 and 60.

It is important to note that in accordance with this invention both $V_I$ and $V_O$ are closed when the counter 44 is counting so as to derive the counts Ct#1 from which the maximum pressure $P_A$ is determined or when the counter 44 is deriving Ct#2 from which the minimum pressure $P_B$ is determined.

If the computer 48 is an HP Model 21 MX, it can be made to perform the READ, FLOW and FEEDBACK functions indicated by the programs at the end of the specification. These functions are performed under the direction of a MAIN PROGRAM, also included at the end of the specification. In accordance with the READ program, Ct#1 is read into the computer 48 when the wave $f_1'$ is decreasing and Ct#2 is read into the computer 48 when $f_1'$ is increasing.

In accordance with the FLOW program, the pressures $P_A$ and $P_B$ are calculated in accordance with the following equations in which the constants A, B and C are calibration constants specific to the particular transducer. They may vary from transducer to transducer, but will remain the same for a given transducer.

$$P_A = A + B(Ct\#1)^2 + C(Ct\#1)^4 \tag{2}$$

$$P_B = A + B(Ct\#2)^2 + C(Ct\#2)^4 \tag{3}$$

In accordance with the FEEDBACK program, the mass flow m for an interval of a duration $\Delta t$ is calculated as indicated by the following expression $$\dot{m} = \frac{V}{RT\Delta t}(P_A - P_B) \tag{4}$$

wherein V is the volume of the first chamber, R is the universal gas constant, T is the absolute temperature indicated by a digital thermometer mounted in the tube 4 and $\Delta t$ is the length of an interval in seconds.

The computer 48 then calculates the time t during which the valve $V_I$ is to be open in accordance with the following well-known proportional integral control algorithm:

$$\begin{aligned} t = &\ K_1 \text{ (Set flow-actual flow)} \\ &+ K_2 \Sigma \text{(Set flow-actual flow)} \\ &+ K_3 \end{aligned} \tag{5}$$

wherein the constants $K_1$, $K_2$ and $K_3$ are such as to provide for optimum performance with the particular combination of mechanical components involved.

The computer 48 outputs the digital number N representing the time t during which $V_I$ is to be open. When this is done, the computer 48 provides a loading pulse l to the load terminal of the downcounter 50, and the number N is transferred to it. The manner in which the open time of the input valve $V_I$ is controlled has already been explained. The maximum time that $V_I$ is to be open is one-quarter of a cycle, and the number N corresponding to this time is such that it equals the number of cycles of $f_8$ occurring during one quarter-cycle.

If a lower flow or pressure is called for, the number N will be less so that the output of the downcounter 50 ceases to be positive at times indicated by the dashed lines 58 and 60 of the graph DC. The valve $V_I$ closes at this time, so that the pressure in the first chamber follows the dotted line 62 in the graph P. The pressure in the chamber is therefore constant for the last part of $Q_1$ as well as for all of $Q_2$.

MAIN PROGRAM

```
 1        ASMB,L
 2             NAM FRED1
 3             ENT RESF,SAVR
 4             ENT TRANS,PROG
 5             EXT READ,FLOW,FEDBK,DSPLY,CLRIO
 6             EXT .DTA.,.DIO.,.PID.,.IIO.,ISSW,.IOR.,.IOC.
 7             COM CNTS1(2),CNTS2(2),RATE(2),PAVE(2),P0(2),P1(2),P2(2)
 8             COM FLC(2),KP(2),KI(2),KD(2),ESUM(2),ACT(2),SET(2),EPR1(2)
 9             COM M/P
10             COM NRS,N,M1
11             COM TRAN,NOSPL
12             COM NFLOW,M
13             CLF 00
14             JSB CLRIO
15             DEF *+1
16        A1   LDA OUT
17             CLB
18             JSB .DIO.
19             DEF A2
20             DEF A3
21             JSB .DTA.
22        A3   JMP A4
23        A2   ASC 11,("INPUT FLC,P0,P1,P2")
24        A4   LDA IN
25             CLB,INB
26             JSB .DIO.
27             OCT 0
28             DEF B1
29             JSB .PID.
30             DEF FLC
31             JSB .RIO.
32             DEF P0
33             JSB .RIO.
34             DEF P1
35             JSB .RIO.
36             DEF P2
37        B1   LDA OUT
38             CLB
39             JSB .DIO.
40             DEF B2
41             DEF B3
42             JSB .DTA.
43        B3   JMP B4
44        B2   ASC 15,("INPUT M CONTROL CSTS KPM,K")
45        B4   LDA IN
46             CLB,INB
47             JSB .DIO.
48             OCT 0
49             DEF C1
50             JSB .RIO.
51             DEF KP
52             JSB .RIO.
53             DEF KI
54             JSB .RIO.
55        C1   LDA OUT
56             CLB
57             JSB .DIO.
58             DEF C2
59             DEF C3
60             JSB .DTA.
61        C3   JMP C4
62        C2   ASC 7,("INPUT NRS ")
```

```
63      C4      LDA IN
64              CLB,INB
65              JSB .DIO.
66              OCT 0
67              DEF D1
68              JSB .JIO.
69              DEF NRS
70      D1      LDA OUT
71              CLB
72              JSB .DIO.
73              DEF D2
74              DEF D3
75              JSB .DTA.
76      D3      JMP D4
77      D2      ASC 17,("INPUT 0 FOR M,1 FOR P CONTROL ")
78      D4      LDA IN
79              CLB,INB
80              JSB .DIO.
81              OCT 0
82              DEF E1
83              JSB .IIO.
84              DEF M/P
85      E1      LDA OUT
86              CLB
87              JSB .DIO.
88              DEF E2
89              DEF E3
90              JSB .DTA.
91      E3      JMP E4
92      E2      ASC 24,("INPUT SETPOINT 0 TO INITIALIZE,1 TO CONTINUE")
93      E4      LDA IN
94              CLB,INB
95              JSB .DIO.
96              OCT 0
97              DEF G1
98              JSB .RIO.
99              DEF SET
100             JSB .JIO.
101             DEF INIT
102     G1      LDA OUT
103             CLB
104             JSB .DIO.
105             DEF G2
106             DEF G3
107             JSB .DTA.
108     G3      JMP G4
109     G2      ASC 23,("INPUT NFLOW,1 FOR FLOW PROGRAM,0 FOR OTHER")
110     G4      LDA IN
111             CLB,INB
112             JSB .DIO.
113             OCT 0
114             DEF G5
115             JSB .IIO.
116             DEF NFLOW
117     G5      LDA NFLOW
118             SLA
119             JMP F0
120             JMP F1
121     F0      LDA OUT
122             CLB
123             JSB .DIO.
124             DEF L2
125             DEF L3
126             JSB .DTA.
127     L3      JMP L4
128     L2      ASC 9,("INPUT SET2,RAT")
```

```
129     L4      LDA IN
130             CLB,INB
131             JSB .DIO.
132             OCT 0
133             DEF L5
134             JSB .RIO.
135             DEF SET2
136             JSB .RIO.
137             DEF RAT
138     L5      DLD RAT
138.1           FDV NCTS
139             DST CONST
140     F1      LDA OUT
141             CLB
142             JSB .DIO.
143             DEF F2
144             DEF F3
145             JSB .DTA.
146     F3      JMP F4
147     F2      ASC 24,(" INPUT NDSPL(=1 FOR DSPLY,=0 FOR OTHER MODE)")
148     F4      LDA IN
149             CLB,INB
150             JSB .DIO.
151             OCT 0
152             DEF E5
153             JSB .JID.
154             DEF NDSPL
155     E5      NOP
156             CLA
157             OTA 1
158             STC 1,C
159             LDA INIT
160             SZA                 IF A=0 INITIALIZE, OTHERWISE CONTINUE
161             JMP CONT2
162             CLA
163             CLB
164             DST ESUM
165     CONT2   NOP
166             CLA
167             STA N
168             STA TRAN
169             STA NBUFF
169.1           STA M
170             LDA PTR
171             STA PT
172             LDA N1
173             ADA N1
174             CMA,INA
175             ADA PTR
176             ADA NTS
177             ADA NTS
178             ADA NTS
179             ADA NTS
180             STA END
181             DLD SET
182             DST TSET
183             LDA CHNL1,I
184             STA INT
185             LDA LOC2
186             STA CHNL2
187             ORB
188     LINK2   DEF READ
189             ORR
190             STF 00
191             STC CHNL2,C
```

```
192            CLC  CHNL3
193            CLC  CHNL4
194            CLC  CHNL5
195            CLC  CHNL6
196            NOP
197            NOP
198    EXEC    NOP
199            LDA  NDSPL
200            SZA
201            JMP  DSPL
202            LDA  N5        TRANSIENT MODE
203            JSB  ISSW
204            SSA
205            JMP  V1
206            JMP  V3
207    V1      LDA  N1
208            STA  TRAN
208.1  V3      LDA  NFLOW
208.2          SZA
208.3          JMP  V2
208.4          JMP  DSPL
208.5  V2      LDA  N6
208.6          JSB  ISSW
208.7          SSA
208.8          STA  M
209    DSPL    LDA  NBUFF
210            SZA
211            JSB  TTY1
212            LDA  N
213            NOP
214            NOP
215            CPA  NRS
216            JSB  TTY
217            JMP  EXEC
218    TTY     NOP
219            CLA
220            STA  N
221            DLD  RATE
222            DST  TRATE
223            DLD  PAVE
224            DST  TPAVE
225            LDA  OUT
226            CLB
227            JSB  .DIO.
228            DEF  FMT
229            DEF  EOL
230            DLD  TRATE
231            JSB  .IOR.
232            DLD  TPAVE
233            JSB  .IOR.
234    EOL     JSB  .DTA.
235            NOP
236            NOP
237            JMP  TTY,I
238    STATS   NOP
239            LDA  OPSTS
240            IOR  OUT
241            JSB  .IOC.
242            NOP
243            SSA
244            JMP  *-3
245            JMP  STATS,I
246    TRANS   NOP
247            DLD  RATE
248            DST  PT,I
```

```
249            ISZ PT
250            ISZ PT
251            DLD PAVE
252            DST PT,I
253            ISZ PT
254            ISZ PT
255            LDA END          CHECK FOR END OF BUFFER
256            CMA,INA
257            ADA PT
258            SSA
259            JMP TR1
260            CLA
261            STA TRAN
262            LDA NI
263            STA NBUFF
264            CLA
265            STA N
266    TR1     JMP TRANS,I
267    TTY1    NOP
268            CLA
269            STA NBUFF
270.           LDA PTR
271            STA PT
272            LDA OUT
273            CLB
274            JSB .OTO.
275            DEF FMT
276            DEF A7
277    A6      DLD PT,I
278            JSB .IOR.
279            ISZ PT
280            ISZ PT
281            DLD PT,I
282            JSB .IOR.
283            ISZ PT
284            ISZ PT
285            LDA END
286            CMA,INA
287            ADA PT
288            SSA
289            JMP A6
290    A7      JSB .DTA.
291            CLA
292            STA N
292.1          LDA PTR
292.2          STA PT
293            JMP TTY1,I
294    PROG    NOP
295            DLD SET
296            FAD CONST
297            DST SET
298            FSB SET2
299            SSA
300            JMP T1
301            CLA
302            STA M
303            DLD TSET
304            DST SET
305    T1      JMP PROG,I
306    FMT     ASC 9,(1X,F7.3,1X,F7.3)
307    LOC2    JSB LINK2,I
308    SAVR    NOP
309            STA SAVEA
310            STB SAVEB
311            ERA,ALS
312            SOC
```

```
313            INA
314            STA  SAVEO
315            JMP  SAVR,I
316     RESR   NOP
317            LDA  SAVEO
318            CLO
319            SLA,ELA
320            STO
321            LDA  SAVEA
322            LDB  SAVEB
323            JMP  RESR,I
324     PTR    DEF  START
325     OPSTS  OCT  40000
326     KPM    BSS  2
327     KIM    BSS  2
328     KOM    BSS  2
329     KPP    BSS  2
330     KIP    BSS  2
331     KDP    BSS  2
332     N5     DEF  5
333     OUT    DEF  7B
334     IN     DEF  1B
335     NONE   DEF  0
336     N1     DEF  1
337     N2     DEF  2
338     N3     DEF  3
339     N4     DEF  4
340     N6     DEF  6
341     INIT   BSS  1
342     INT    BSS  1           STORE CONTENT OF MEMORY ADD. 11
343     SAVEA  BSS  1
344     SAVEB  BSS  1
345     SAVEO  BSS  1
346     TRATE  BSS  2
347     TPAVE  BSS  2
348     START  BSS  200
349     END    BSS  1
350     PT     BSS  1
351     NBUFF  BSS  1
352     NTS    DEC  50
353     TSET   BSS  2
354     SET2   BSS  2
355     RAT    BSS  2
356     CONST  BSS  2
357     NCTS   DEC  300.0
358     CHNL1  EQU  11B
359     CHNL2  EQU  10B
360     CHNL3  EQU  12B
361     CHNL4  EQU  15B
362     CHNL5  EQU  13B
363     CHNL6  EQU  14B
364            END
```

READ

```
1       ASMB,L
2              NAM  READ
3              ENT  READ
4              EXT  .PACK,ISSW
5              EXT  FLOW,FEDBK,DSPLY
6              EXT  SAVR,RESR
7              EXT  TRANS,PROG
8       READ   NOP
9              COM  CNTS1(2),CNTS2(2),RATE(2),PAVE(2),P0(2),P1(2),P2(2)
```

```
10          COM FLC(2),KP(2),KI(2),KD(2),FSUM(2),ACT(2),SET(2),ERRI(2)
11          COM M/P
12          COM NRS,N,M1
13          COM TRAN,NDSPL
14          COM NFLOW,M
15          CLF 0
16          JSB SAVR
17          LIB CHNL,C       INPUT 16 LSB BITS FROM TRANSDUCER
18          STB AA
19          LDA LOC3
20          STA CHNL
21          JSB RESR
22          STC CHNL,C
23          STF 0
24          JMP READ,I
25   READA  NOP
26          CLF 0
27          JSB SAVR
28          LDB AA
29          LIA CHNL,C       INPUT 5 MSB FROM TRANSDUCER
30          CMA              CONVERT FROM NEGATIVE TRUE LOGIC
31          CMB
32          AND MASK
33          PHL
34          CLE,ERA
35          ERB
36          JSB .PACK        CONVERT BINARY DATA TO FLOATING POINT
37          DEC 31
38          DST CNTS1
39          LDA LOC1
40          STA CHNL
41          JSB RESR
42          STC CHNL,C
43          STF 0
44          JMP READA,I
45   LOC2   JSB LINK2,I
46   LOC1   JSB LINK3,I
47   LOC3   JSB LINK4,I
48   LOC4   JSB LINK5,I
49          ORB
50   LINK2  DEF READ
51   LINK3  DEF DATA2
52   LINK4  DEF READA
53   LINK5  DEF DATAA
54          ORR
55   DATA2  NOP
56          CLF 0
57          JSB SAVR
58          NOP
59          LIB CHNL,C       INPUT LSB
60          STB AA
61          LDA LOC4
62          STA CHNL
63          JSB RESR
64          STC CHNL,C
65          STF 0
66          JMP DATA2,I
67   DATAA  NOP
68          CLF 0
69          JSB SAVR
70          LDB AA
71          LIA CHNL,C       INPUT MSB
72          CMA              NEGATIVE TRUE LOGIC
73          CMB
74          AND MASK
```

```
75           PUL
76           CLE,ERA
77           ERB
78           JSB .PACK        CONVERT TO FLOATING POINT
79           DEC 31
80           DST CNTS2        CHECK FOR PROPER TIMING CNTS2>CNTS1
81           DLD ERR1
82           SZA
83           JMP A1
84           DLD CNTS1
85           FSB CNTS2
86           SSA
87           JMP T1
88           DLD CNTS2
89           DST CNTS1
90           LDA LOC1
91           STA CHNL
92           JSB RESR
93           STC CHNL,C
94           STF 0
95           JMP DATAA,I
96     A1    DLD CNTS1
97           FSB CNTS2
98           SSA,RSS
99           JMP T1
100          DLD CNTS2
101          DST CNTS1
102          LDA LOC1
103          STA CHNL
104          JSB RESR
105          STC CHNL,C
106          STF 0
107          JMP DATAA,I
108    T1    LDA LOC2
109          STA CHNL
110          NOP
111          JSB .FLOW        CALCULATE RATE AND PAVE
112          NOP
113          LDA M/P          =1 FOR MASS FLOW CONTROL, 1FOR PRESSURE
114          SZA              IF A=0, DO P+2,OTHERWISE P+1
115          JMP CONT3
116          DLD RATE
117          DST ACT
118          JMP CONT4
119    CONT3 DLD PAVE
120          DST ACT
121    CONT4 LDA NDSPL
122          SLA
123          JMP TR2          NDSPL=1
124          LDA M
125          SSA
126          JSB PPOG
127    TR4   JSB FEDBK        CALCULATE AND OUTPUT 16BIT DUTY CYCLE
128          LDA TRAN
129          SLA
130          JSB TRANS            TRAN=1
131          JMP TR3              TRAN =0
132    TR2   JSB FEDBK
133          JSB DSPLY
134    TR3   ISZ N            INCREMENT N
135          JSB RESR
136          STC CHNL,C
137          STF 0
138          JMP DATAA,I
139    MASK  OCT 77
```

```
140        CHNG   EQU 10B
141   AA          BSS 1
142   N6          DEF 6
143              END
144   END$
145
```

FLOW

```
1    ASMB,L
2              NAM FLOW
3              ENT FLOW
4    FLOW      NOP
5              COM CNTS1(2),CNTS2(2),RATE(2),PAVE(2),P0(2),P1(2),P2(2)
6              COM FLC(2),KP(2),KI(2),KD(2),ESUM(2),ACT(2),SET(2),ERR1(2)
7              DLD P2
8              FMP CNTS1
9              FAD P1
10             FMP CNTS1
11             FAD P0
12             DST PA         PA=P0+P1*CNTS1+P2*CNTS1*CNTS1
13             DLD P2
14             FMP CNTS2
15             FAD P1
16             FMP CNTS2
17             FAD P0
18             DST PB         PB=P0+P1*CNTS2+P2*CNTS2*CNTS2
19             DLD ERR1
20             SZA,RSS
21             JMP A1
22             DLD PB
23             FSB PA
24             FMP FLC
25             DST RATE       RATE=FLC*(PA-PB)
26             DLD PA
27             FAD PA
28             FSB PB
29             DST PAVE
30             JMP A2
31   A1        DLD PA
32             FSB PB
33             FMP FLC
34             DST RATE
35             DLD PB
36             FAD PB
37             FSB PA
38             DST PAVE
39   A2        NOP
40             JMP FLOW,I
41   CST1      DEC 3.3333E-1
42   PA        BSS 2
43   PB        BSS 2
44             END
45   END$
```

FEEDBACK

```
1    ASMB,L
2              NAM FEDBK
3              ENT FEDBK
4    FEDBK     NOP
5              COM CNTS1(2),CNTS2(2),RATE(2),PAVE(2),P0(2),P1(2),P2(2)
6              COM FLC(2),KP(2),KI(2),KD(2),ESUM(2),ACT(2),SET(2),ERR1(2)
```

```
 7            OLD  ACT1
 8            FMP  .9
 9            DST  ACT1
10            OLD  ACT
11            FMP  .1
12            FAD  ACT1
13            DST  ACT1
14            NOP
15            NOP
16            NOP
17            NOP
18            OLD  SET
19            FSB  ACT1
20            DST  E            E=SETPOINT-ACTUAL
21            FAD  ESUM
22            DST  ESUM         ESUM=E+ESUM
23            SSA
24            JMP  LIMIT
25            OLD  CST2
26            FSB  ESUM
27            SSA
28            JMP  LIM2
29     LIM    NOP
30            OLD  E
31            FMP  KP
32            DST  PROP         PROP=E*KP*ERR1/ACT1
33            OLD  ESUM
34            FMP  KI
35            DST  INTEG        INTEG=ESUM*KI*ERR1/PAVE1*FLC*DT
36            FAD  PROP
37            SSA
38            JMP  NEG
39            FIX
40            FOT
41     RET    DST  ERR1
42            FAD  OFSET
43            FIX
44     OUTPT  CMA
45            OTA  CHL
46            JMP  FEDBK,I
47     NEG    CLA
48            CLB
49            JMP  RET
50     LIMIT  CLA
51            CLB
52            DST  ESUM
53            JMP  LIM
54     LIM2   OLD  CST2
55            DST  ESUM
56            JMP  LIM
57     OFSET  DEC  7.5E3
```

What is claimed is:

1. Apparatus for controlling the flow of a gas so as to maintain a constant mass flow to a load, comprising a first valve having an input to which gas under pressure may be applied and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration $\Delta t$, means defining a reference volume $R_V$, a second valve having an input coupled to the outlet port of said volume V and an output coupled to said reference volume $R_V$, means placing said second valve in a closed position during the said first portion of each cycle, for a second portion occurring immediately thereafter, and during the last portion of each cycle and placing said second valve in an open position between the second and last portions of each cycle, a third valve having an input coupled to said reference volume $R_V$ and an output to which a load can be coupled, means for placing said third valve in an open position when said second valve is closed and placing said third valve in a closed position when said second valve is open, means activating said pressure signal producing means during the second portion of each cycle so as to produce a signal representing the pressure $P_A$ in said volume V when said first and second valves are closed, means activating said pressure signal producing means during the last portion of each cycle so as to produce a signal representing the pressure $P_B$ in said volume V when said first and second valves are closed, means responsive to the signals $P_A$ and $P_B$ for deriving a control signal representing the mass flow m through the volume V equal to $$(P_A - P_B)/\Delta t \cdot V/RT$$

wherein R is the universal gas constant and T is the temperature of the gas in the volume V, and control means responsive to said control signal for controlling the flow of gas through said first valve so as to maintain the mass flow m at a predetermined set value.

2. Apparatus for controlling the flow of a gas so as to maintain a constant pressure on a load, comprising a first valve having an input to which gas under pressure may be applied and an output, means defining a volume V having an inlet port coupled to the output of said first valve and an outlet port, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, each cycle having a duration $\Delta t$, means defining a reference volume $R_V$, a second valve having an input coupled to the outlet port of said volume V and an output coupled to said reference volume $R_V$, means placing said second valve in a closed position during the said first portion of each cycle, for a second portion occurring immediately thereafter, and during the last portion of each cycle and placing it in an open position between the second and last portions of each cycle, a third valve having an input coupled to said reference volume $R_V$ and an output to which a load can be coupled, means placing said third valve in an open position when said second valve is closed and placing it in a closed position when said second valve is open, means activating said pressure signal producing means during the second portion of each cycle so as to produce a signal representing the pressure $P_A$ in said volume V when said first and second valves are closed, means activating said pressure signal producing means during the last portion of each cycle so as to produce a signal representing the pressure $P_B$ in said volume V when said first and second valves are closed, and means coupled to said signal producing means for controlling the flow of gas through said first valve so as to keep a pressure $P_C$ in said reference volume equal to a predetermined set pressure, the pressure $P_C$ being equal to $$P_B - (mRT/R_V)$$

wherein m equals $$(P_A - P_B)/\Delta t \cdot V/RT$$

R is the universal gas constant and T is the absolute temperature.

3. Apparatus for controlling the flow of a gas so as to maintain a constant pressure on a load, comprising a first valve having an input to which gas under pressure may be applied and an output, means defining a volume V having an inlet port coupled to the output of said first valve and an outlet port to which a load may be coupled, pressure signal producing means including a transducer for producing, when activated, an electrical signal representing the pressure in said volume V, means for placing said first valve in an open position during a first portion of each of a plurality of successive cycles and for placing it in a closed position during the remainder of each cycle, means defining a reference volume $R_V$, a second valve having an input coupled to the outlet port of said volume and an output coupled to said reference volume $R_V$, means placing said second valve in a closed position during the said first portion of each cycle, for a second portion occurring immediately thereafter, and during the last portion of each cycle and placing said second valve in an open position between the second and last portions of each cycle, a third valve having an input coupled to said reference volume $R_V$ and an output to which a load can be coupled, means for placing said third valve in an open position when said second valve is closed and placing said third valve in a closed position when said second valve is open, means activating said pressure signal producing means during the second portion of each cycle or the last portion of each cycle, and control means responsive to the signal produced in each cycle by said pressure signal producing means for controlling the flow of gas through said first valve so as to maintain the pressure which the signal from said pressure signal producing means represents at a predetermined set value.

4. Apparatus as set forth in claim 3 wherein said means for activating said pressure signal producing means is activated only during the last portion of each cycle, and said control means responds to the signal produced by said pressure signal producing means at the last portion of each cycle to control the flow of gas through said first valve so as to maintain the said pressure at a predetermined set value.

* * * * *

UNITED STATES PATENT OFFICE
CERTIFICATE OF CORRECTION

Patent No. 4,437,489　　　　　Dated March 20, 1984

Inventor(s)　　Michael A. Casale

It is certified that error appears in the above-identified patent and that said Letters Patent are hereby corrected as shown below:

| | | |
|---|---|---|
| Column 1 | line 21 | "m" should read -- $\dot{m}$ -- |
| Column 3 | line 22 | "l" should read -- $\ell$ -- |
| | line 36 | "$f_1$" (second occurrence) should read -- $\overline{f_1}$ -- |
| | line 43 | "$f_1$" (first occurrence) should read -- $\overline{f_1}$ -- |
| Column 4 | line 24 | "m" should read -- $\dot{m}$ -- |
| | line 48 | "l" should read -- $\ell$ -- |
| Column 25 | line 20 | "m" should read -- $\dot{m}$ -- |
| | line 23 | "$(P_A-P_B)\Delta t \cdot V/RT$" should read -- $[(P_A-P_B)\Delta t]\cdot V/RT$ -- |
| | line 29 | "m" should read -- $\dot{m}$ -- |
| Column 26 | line 10 | "$P_B-(mRT/R_V)$" should read -- $P_B-(\dot{m}RT/R_V)$ -- |
| | line 12 | "m" should read -- $\dot{m}$ -- |
| | line 14 | "$(P_A-P_B)\Delta t \cdot V/RT$" should read -- $[(P_A-P_B)\Delta t]\cdot V/RT$ -- |

Signed and Sealed this

Twenty-first Day of August 1984

[SEAL]

Attest:

Attesting Officer

GERALD J. MOSSINGHOFF

Commissioner of Patents and Trademarks